(12) United States Patent
Kagawa et al.

(10) Patent No.: US 8,357,776 B2
(45) Date of Patent: Jan. 22, 2013

(54) COMPOSITION FOR SUPPRESSING RE-ELEVATION OF CHOLESTEROL, AND USAGE THEREOF

(75) Inventors: Kyoichi Kagawa, Ibaraki (JP); Chizuko Fukuhama, Kawanishi (JP)

(73) Assignee: MG Pharma Inc., Ibaraki-shi (JP)

( * ) Notice: Subject to any disclaimer, the term of this patent is extended or adjusted under 35 U.S.C. 154(b) by 1500 days.

(21) Appl. No.: 11/600,820

(22) Filed: Nov. 17, 2006

(65) Prior Publication Data

US 2007/0191282 A1      Aug. 16, 2007

(30) Foreign Application Priority Data

Nov. 17, 2005   (JP) .................................. 2005-333288

(51) Int. Cl.
*A61K 38/04*   (2006.01)
*A61P 3/06*   (2006.01)
*C12Q 1/60*   (2006.01)
*G01N 33/92*   (2006.01)

(52) U.S. Cl. .......... 530/330; 514/21.9; 514/7.4; 435/11; 436/71

(58) Field of Classification Search .................. None
See application file for complete search history.

(56) References Cited

U.S. PATENT DOCUMENTS

| 5,723,443 | A | 3/1998 | Kagawa et al. | 514/18 |
| 5,756,467 | A | 5/1998 | Kagawa et al. | 514/18 |
| 5,958,885 | A * | 9/1999 | Kagawa et al. | 514/18 |
| 6,046,168 | A | 4/2000 | Kagawa et al. | 514/16 |
| 2004/0009216 | A1 * | 1/2004 | Rodrigueza et al. | 424/450 |

FOREIGN PATENT DOCUMENTS

| EP | 0420979 | 1/1994 |
| EP | 0838474 | 3/2005 |
| JP | 5-87052 | 12/1993 |
| JP | 6-293796 | 10/1994 |
| JP | 7-188284 | 7/1995 |
| JP | 9-255698 | 9/1997 |
| JP | 11-263733 A | 9/1999 |
| WO | WO 84/03202 | 8/1984 |
| WO | WO 89/06970 | 8/1989 |
| WO | WO 97/00890 | 1/1997 |
| WO | WO 97/35875 | 10/1997 |

OTHER PUBLICATIONS

Ansell, Curr Atheroscler Rep. Feb. 2005;7(1):29-33.*
Retrieved from from Website: http://forum.lowcarber.org/archive/index.php/t-186814.html, 2 pages, 2004 [retrieved on Dec. 21, 2010].*
Stone, 2004, Circulation, 110, 2280-2282.*
Japanese Office Action dated Feb. 10, 2009 (in Japanese).
Kagawa et al; Suppressive Effect of Globin Digest on Postprandial Hyperlipidemia in Male Volunteers[1,2]; J. Nutr. 128, (1998) pp. 56-60.
Kagawa et al; Globin Digest, Acidic Protease Hydrolysate, Inhibits Dietary Hypertriglyceridemia . . . Most Superior Effect; Life Sciences 58 (1996) pp. 1745-1755.
Kagawa et al; "Hypotriglyceridemic Effect of Globin Digest on Subjects with Borderline Hyperlipidemia;" J. Jpn. Soc. Nutr. Food Sci. 52 (1999); pp. 71-77.

* cited by examiner

*Primary Examiner* — Karlheinz R Skowronek
*Assistant Examiner* — Satyanarayana R Gudibande
(74) *Attorney, Agent, or Firm* — Kratz, Quintos & Hanson, LLP (57) ABSTRACT

The present invention provides a composition (composition for suppressing re-elevation of cholesterol) that has the effects of suppressing re-elevation of cholesterol in patients with high cholesterol or pre-high cholesterol, and that can therefore be used to suppress re-elevation of cholesterol in those patients. The present invention also provides a composition which, due to the effects described above, can be used to prevent or treat conditions or diseases caused by high cholesterol due to cholesterol re-elevation, specifically hypercholesterolemia, arteriosclerosis and diseases and conditions stemming therefrom. The composition of this invention uses as an active component an edible protein hydrolysate, preferably a globin proteolysate or a peptide consisting of Val-Val-Tyr-Pro.

4 Claims, 5 Drawing Sheets

FIG. 5

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Peptide found in globulin hydrolysate

<400> SEQUENCE: 1

Val Val Tyr Pro
  1
```

COMPOSITION FOR SUPPRESSING RE-ELEVATION OF CHOLESTEROL, AND USAGE THEREOF

This patent application claims priority from a Japanese Patent Application (Application No. 2005-333288) filed on Nov. 17, 2005.

TECHNICAL FIELD

The present invention relates to a composition that can be used favorably in patients with high cholesterol or pre-high cholesterol, and that is used for suppressing re-elevation of cholesterol and maintaining blood cholesterol levels in the appropriate range during a drug rest period following treatment (such as administration of statin drugs or the like) to lower the patients' cholesterol.

The present invention also relates to a method for suppressing re-elevation of cholesterol and maintaining normal blood cholesterol levels in patients at risk for cholesterol re-elevation by using the cholesterol re-elevation suppressing effect of the composition, and to a method for preventing or ameliorating conditions and diseases (such as hypercholesterolemia and arteriosclerosis) which occur due to elevated cholesterol. In particular, the present invention relates to a method for suppressing re-elevation of cholesterol and maintaining blood cholesterol levels in the appropriate range during a drug rest period following treatment (such as administration of statin drugs and the like) to lower cholesterol in patients with high cholesterol or pre-high cholesterol.

BACKGROUND ART

With the adoption of western diets in recent years more high-fat foods have become available, leading to an increase in the incidence of such lifestyle-related diseases as hypercholesterolemia, hyperlipidemia and arteriosclerosis. Symptoms of hyperlipidemia accompanying elevated total blood cholesterol and low-density lipoprotein (LDL) cholesterol are known to be an important risk factor for atherosclerotic cardiovascular disease (Assman, G. et al., Circulation, 1999, 100, 1930 to 1938; Grundy, S. et al., Circulation, 1999, 100, 1134 to 1146).

Methods of reducing blood cholesterol by interfering with the circulation of bile acids through the intestines have been established for ameliorating hyperlipidemia. Specific examples of such methods include treatment with HMG-CoA reductase inhibitors, preferably statin drugs such as simvastatin and fluvastatin, and treatment with bile acid sequestrants such as anion exchange resins.

These drugs are used world-wide as cholesterol-lowering agents (or lipid-lowering agents), and of these, statin drugs command a roughly 80 to 90% share of the market for hyperlipidemia treatment, and their effectiveness has been established as the drugs of choice for hypercholesterolemia. In recent years, however, side-effects such as muscle disorders (rhabdomyolysis), liver function disorders (liver enzyme elevation, etc.), neural disorders and the like have been reported which are common to statin drugs, and there are concerns about safety with long-term use (Clinics in Liver Disease, 2003, 7, 415 to 433; Current Therapy, 1999, Vol. 19, No. 9, 53 to 56; Donaghy M., Neurology, 2002, 58, 1321 to 1322; Gaist, D. et al., Neurology, 2002, 58, 1333 to 1337). Cholesterol levels are also seen to rebound after the drug is stopped, making it difficult to stop the drug. The reality now is that it may be impossible to stop administering statin drugs despite the awareness of side-effects, and if they are stopped patients may be forced to go on low-cholesterol diets, detracting markedly from quality of life.

SUMMARY OF THE INVENTION

It is an object of the present invention to provide a composition and method for suppressing re-elevation of blood cholesterol and maintaining appropriate cholesterol levels in patients at risk of blood cholesterol re-elevation or patients with conditions or diseases caused by elevated cholesterol who have received cholesterol lowering treatment, and particularly patients during a drug rest period in such treatment. It is also an object of the present invention to provide a composition and method for suppressing re-elevation of blood cholesterol and preventing and ameliorating conditions and diseases caused by elevated cholesterol in patients at risk of blood cholesterol re-elevation or patients with conditions or diseases caused by elevated cholesterol who have received cholesterol lowering treatment, and particularly patients during a drug rest period in such treatment.

To achieve these objects, the inventors discovered that when the blood cholesterol of patients with high cholesterol was lowered with statin drug (cholesterol-lowering treatment), statin administration was interrupted, and a globin proteolysate was administered during the subsequent drug rest period, cholesterol levels were maintained within the appropriate range over the long term, even without dietary restrictions. When no globin proteolysate was given during the statin rest period, cholesterol levels rebounded, and a second cholesterol lowering treatment was soon necessary. It was also found that when a globin proteolysate was administered during the statin drug rest period, levels of good cholesterol (HDL cholesterol) in blood rose more than they did after cholesterol lowering treatment.

From these findings, the inventors confirmed that a globin proteolysate has a cholesterol re-elevation-suppressing effect, and particular that use of this globin proteolysate following cholesterol-lowering treatment by statin drug administration or the like is effective for preventing cholesterol re-elevation and maintaining normal blood cholesterol levels over the long term. These findings show that cholesterol re-elevation can be suppressed over the long term by using a globin proteolysate in conjunction with or alternating with cholesterol-lowering treatment by statin drug administration or the like, thereby making it possible to reduce the number of statin drug administrations and thereby reduce the side-effects caused by such drugs. The present invention was perfected based on these findings.

That is, the present invention encompasses the following embodiments.

1. A composition for suppressing re-elevation of cholesterol, comprising an edible protein hydrolysate as an active component.

2. A composition for suppressing re-elevation of cholesterol, comprising a globin proteolysate or a peptide consisting of Val-Val-Tyr-Pro (SEQ ID NO: 1) as an active component.

3. The composition for suppressing re-elevation of cholesterol according to 1 or 2, which is used to treat a patient with high cholesterol or pre-high cholesterol to suppress re-elevation of cholesterol in the patient.

4. The composition for suppressing re-elevation of cholesterol according to any one of 1 through 3, which is used to treat a patient with high cholesterol or pre-high cholesterol either in conjunction with or alternating with cholesterol-lowering treatment for the patient.

5. The composition for suppressing re-elevation of cholesterol according to any one of 1 through 4, which is used to treat a patient with high cholesterol or pre-high cholesterol during a rest period in cholesterol-lowering treatment for the patient.

6. The composition for suppressing re-elevation of cholesterol according to 4 or 5, wherein the cholesterol-lowering treatment is a statin drug administration.

7. The composition for suppressing re-elevation of cholesterol according to any one of 1 through 6, which is a composition for maintaining a total blood cholesterol level in a normal range.

8. The composition for suppressing re-elevation of cholesterol according to any one of 1 through 6, which is used in a coronary disease patient with high cholesterol or pre-high cholesterol to maintain a total cholesterol level within a range at which anti-cholesterol drug administration is not required. A "range at which anti-cholesterol drug administration is not required" is a range at or below the upper limit (220 to 240 mg/dl) of the normal range for total cholesterol.

9. The composition for suppressing re-elevation of cholesterol according to any one of 1 through 8, wherein the composition is a food, drug or feed.

10. The composition for suppressing re-elevation of cholesterol according to 9, which is a food labeled on a package or container thereof cholesterol re-elevation suppressing effects or other effects deriving therefrom.

11. The composition for suppressing re-elevation of cholesterol according to 9 or 10, which is a food for a human with high cholesterol or pre-high cholesterol who is receiving cholesterol-lowering treatment to suppress re-elevation of cholesterol during a rest period following cholesterol-lowering treatment in the human.

12. A composition for preventing or ameliorating a condition or a disease caused by high cholesterol, comprising as an active component the composition for suppressing re-elevation of cholesterol of 1 or 2.

13. The composition according to 12, wherein the condition or disease caused by high cholesterol is hypercholesterolemia, arteriosclerosis, or a disease or condition stemming from these.

14. The composition according to 12 or 13, wherein the composition is a food, drug or feed.

15. The composition according to 14, which is a food having labeled on the package or container thereof preventative or ameliorating effects against conditions or diseases caused by high cholesterol.

16. A method for suppressing re-elevation of cholesterol in a patient with high cholesterol or pre-high cholesterol, comprising administering to the patient the composition of 1 or 2 in a quantity sufficient to produce cholesterol re-elevation suppressing effects.

17. A method for preventing or ameliorating a condition or a disease caused by high cholesterol in a patient with high cholesterol or pre-high cholesterol, comprising administering to the patient the composition of 1 or 2 in a quantity sufficient to produce cholesterol re-elevation suppressing effects.

18. The method according to 16 or 17, comprising administering to a patient with high cholesterol or pre-high cholesterol the composition of 1 or 2 either in conjunction with or alternating with cholesterol-lowering treatment for the patient.

19. The method according to 18, comprising administering to a patient with high cholesterol or pre-high cholesterol the composition of 1 or 2 during a rest period following cholesterol-lowering treatment for the patient.

20. The method according to 18 or 19, wherein the cholesterol-lowering treatment is a statin drug administration.

21. The method according to any one of 16 through 20, for maintaining a total blood cholesterol level in a normal range.

22. The method according to any one of 16 through 20, for maintaining a total blood cholesterol level in a normal range in a coronary disease patient with high cholesterol or pre-high cholesterol.

23. Use of an edible protein hydrolysate and particularly a globin proteolysate or a peptide consisting of Val-Val-Tyr-Pro (SEQ ID NO: 1) to manufacture a composition for suppressing re-elevation of cholesterol of 1 or 2.

24. Use of a composition of 1 or 2, for manufacturing a composition for preventing or ameliorating conditions or diseases caused by high cholesterol.

25. The use according to 23 or 24, wherein the composition for suppressing re-elevation of cholesterol or composition for preventing or ameliorating conditions or diseases caused by high cholesterol is a drug composition, food composition or feed composition.

BEST MODE FOR CARRYING OUT THE INVENTION (1) Definition of Terms

In the present invention, "cholesterol" means cholesterol concentration in blood or serum.

Unless otherwise specified, "hypercholesterolemia" in the present invention includes both hypercholesterolemia in which the total serum cholesterol value is 220 mg/dl or more, and hyper-LDL-cholesterolemia in which the serum LDL cholesterol value is 140 mg/dl or more.

"High cholesterol" in the present invention indicates either a state of elevated blood cholesterol in which total serum cholesterol is 220 mg/dl or more, or a state at the boundary between normal and elevated blood cholesterol in which total serum cholesterol is 200 mg/dl to 220 mg/dl, or a state of elevated blood LDL cholesterol in which serum LDL cholesterol is 140 mg/dl or more, or a state at the boundary between normal and elevated blood LDL cholesterol in which serum LDL cholesterol is 120 mg/dl to 140 mg/dl. In the case of patients suffering from coronary disease (such as angina, myocardial infarction and other forms of ischemic heart disease), however, high cholesterol means either total serum cholesterol of 180 mg/dl or more or serum LDL cholesterol of 100 mg/dl or more.

In the present invention, for cholesterol (or a blood cholesterol value) to be in the normal range or in appropriate levels means that total serum cholesterol is near 220 to 240 mg/dl or less and serum LDL cholesterol is less than 120 mg/dl. In the case of patients suffering from coronary disease (such as angina, myocardial infarction and other forms of ischemic heart disease), however, for cholesterol (or a blood cholesterol value) to be in the normal range means that total serum cholesterol is less than 180 mg/dl and serum LDL cholesterol is less than 100 mg/dl.

(2) Composition for Suppressing Re-elevation of Cholesterol

The composition for suppressing re-elevation of cholesterol of the present invention contains as an active ingredient an edible protein hydrolysate, particularly a globin proteolysate or a peptide (Val-Val-Tyr-Pro) (SEQ) ID NO: 1).

This edible protein hydrolysate can be manufactured using as the raw material animal proteins such as fish powder or globin or plant proteins such as corn protein (zein) or soy protein.

A globin proteolysate here means a hydrolysate of a globin protein such as hemoglobin or myoglobin. There are no particularly limits on the type of animal used as the source of this globin protein. For example, a blood source such as cows, pigs, sheep, humans or horses can be used as the protein source. A meat such as animal meat or fish meat containing large quantities of myoglobin can also be used as the protein source.

Operations for hydrolyzing edible proteins and particularly globin proteins can be in accordance with the methods described in International Publication No. WO89/06970. Hydrolysis is normally accomplished using hydrolytic enzymes such as 1 or 2 or more kinds of acidic protease, neutral protease or alkaline protease.

For example, one method for hydrolyzing a globin protein is to first disperse globin protein-containing material in water to a concentration of 5 to 30% by weight (as solids), adjust the pH with acid or alkali to the optimal pH for the protease, and then add the protease either all at once or gradually and react the enzyme for 3 to 48 hours at a temperature of 20 to 70° C.

The protein hydrolysate (globin proteolysate) obtained in this way can be prepared as the composition for suppressing re-elevation of cholesterol having cholesterol re-elevation suppressing action of the present invention, either as is, or after drying, or after addition of a suitable amount of an extender such as carboxymethyl cellulose or dextrin, followed by drying and solidification.

Moreover, since the peptide (Val-Val-Tyr-Pro) (SEQ ID NO: 1) used in the present invention constitutes roughly 1% by weight of the globin proteolysate, it can be isolated and refined from the globin proteolysate.

Any known method for purifying proteins or peptides can be adopted as the isolation and purification method. For example, a fraction containing the peptide (Val-Val-Tyr-Pro) (SEQ ID NO: 1) can be obtained by a suitable combination of salting out, dialysis, ion exchange resin, ultrafiltration, reverse-phase chromatography and the like, and the peptide (Val-Val-Tyr-Pro) (SEQ ID NO: 1) can be further isolated from this fraction. Of these purification methods, reverse-phase chromatography is preferably performed as a combination of reverse-phase chromatography under acidic conditions and reverse-phase chromatography under neutral conditions.

The amount of protein in the fraction can be measured by a known protein assay method such as the ninhydrin method. The amino acid sequence of the protein contained in the selected fraction can be determined by a known method (amino acid analysis), thereby confirming the presence of a peptide comprising the Val-Val-Tyr-Pro (SEQ ID NO: 1) amino acid sequence that is the target of the present invention. The peptide (Val-Val-Tyr-Pro) (SEQ ID NO: 1) may be one that has been isolated and purified by the method described above, but the fraction containing it can also be used as an active component in the composition for suppressing cholesterol re-elevation of the present invention as long as it has a cholesterol re-elevation suppressing effect.

This peptide (Val-Val-Tyr-Pro) (SEQ ID NO: 1) can also be prepared by chemical synthesis using known protein synthesis methods. Examples of protein synthesis methods include the azide method, acid chloride method, acid anhydride method, mixed acid anhydride method, DCC method, active ester method, carboimidazole method, oxidation-reduction method, DCC-additive (HOMB, HOBt, HOSu) method ("The Peptide" Vol. 1(1966), Schreder & Luhke, Academic Press, New York, USA; or "Peptide Gosei", Izumiya et al., Maruzen (1975), etc.) or the like. Peptide synthesis may be by solid-phase synthesis or liquid-phase synthesis using these methods.

In these peptide synthesis methods, it is desirable to protect the functional group of an amino acid (such as tyrosine or threonine) having a side-chain functional group. Protective groups that can be used include such known protective groups as benzyloxycarbonyl (Cbz-), t-butoxycarbonyl (Boc-) and benzyl (Bz-) groups and the like. This protective group can be deprotected by a known method in the peptide synthesis process of the present invention.

The composition for suppressing re-elevation of cholesterol of the present invention can be used effectively as a drug composition, food composition or feed composition based on its cholesterol re-elevation suppressing effect. The make-up and use of each composition is explained below.

(2-1) Drug Composition and Use

The drug composition of the present invention contains a quantity of an edible protein hydrolysate (particularly a globin proteolysate or a peptide (Val-Val-Tyr-Pro) (SEQ ID NO: 1)) sufficient to produce a cholesterol re-elevation suppressing effect. The drug composition of the present invention has a cholesterol re-elevation-suppressing effect attributable to the edible protein hydrolysate (particularly globin proteolysate or a peptide (Val-Val-Tyr-Pro) (SEQ ID NO: 1) by means of which conditions and diseases caused by re-elevation of blood cholesterol can be prevented or ameliorated.

Therefore, the drug composition of the present invention can be used effectively with the aim of suppressing re-elevation of cholesterol (as a cholesterol re-elevation suppressor for example), or as a preventative or ameliorative for various conditions or diseases caused by high cholesterol.

Conditions or diseases caused by high cholesterol here include hypercholesterolemia (including hyper-LDL-cholesterolemia), arteriosclerosis, and various diseases stemming from arteriosclerosis. Arteriosclerosis in this case includes atherosclerosis. Examples of various diseases stemming from arteriosclerosis included cerebrovascular diseases such as cerebral infarction and cerebral hemorrhage and heart diseases such as myocardial infarction and angina.

The drug composition of the present invention may consist of only the edible protein hydrolysate described above, and particularly of the globin proteolysate or a peptide (Val-Val-Tyr-Pro) (SEQ ID NO: 1) by itself. As discussed above, however, the drug composition of the present invention may be any that contain the aforementioned edible protein hydrolysate and particularly the globin proteolysate or a peptide (Val-Val-Tyr-Pro) (SEQ ID NO: 1) in an amount sufficient to produce a cholesterol re-elevation suppressing-effect, and is normally prepared with pharmacologically acceptable carriers or additives in addition to the active component described above.

Carriers in this case include excipients, diluents, binders, humectants, disintegrants, disintegration inhibitors, absorbefacients, lubricants, solubilizers, buffers, emulsifiers, suspending agents and the like that are commonly used according to the administered form of the drug composition (preparation). Examples of additives include stabilizers, preservatives, buffers, isotonic agents, chelating agents, pH adjusters, surfactants, colorants, perfumes, flavorings, sweeteners and the like that are commonly used according to the administered form of the drug composition (preparation).

The drug composition of the present invention may also be compounded with other cholesterol-lowering agents in addition to an edible protein hydrolysate and particularly a globin proteolysate or the peptide (Val-Val-Tyr-Pro) (SEQ ID NO: 1) as the active component.

The administered unit form (drug preparation form) of the drug composition may be selected from a variety of forms according to the administration route, and these can be generally classified into preparations for oral administration, nasal administration, sublingual administration, parenteral administration (injections, drips) and the like. These can be compounded, molded and prepared by ordinary methods into a solid administration form such as tablets, pills, powder, granules or capsules or a liquid administration form such as a solution, suspension, emulsion, syrup or elixir. They can also be prepared as dried products that can be converted into liquid form before use by addition of an appropriate carrier. All these can be prepared by ordinary methods.

When the drug composition of the present invention is prepared with such carriers or additives, the proportion of the edible protein hydrolysate and particularly the globin proteolysate or the peptide (Val-Val-Tyr-Pro) (SEQ ID NO: 1) in the drug composition is not particularly limited but is normally about 0.5% to less than 100% by weight for the globin proteolysate or about 0.005% to less than 100% by weight for the peptide (Val-Val-Tyr-Pro) (SEQ ID NO: 1).

The dosage of the drug composition of the present invention can be selected appropriately according to the purpose of the drug composition (cholesterol re-elevation suppression, prevention or amelioration of conditions or diseases caused by high cholesterol due to cholesterol re-elevation), the method of administering the composition, the administered form, and the age, weight and symptoms (degree of high cholesterol) of the patients to whom it is administered. In general, the dosage of the edible protein hydrolysate and particularly the globin proteolysate or the peptide (Val-Val-Tyr-Pro) (SEQ ID NO: 1) is preferably in the range of about 100 mg to 3,000 mg or 1 mg to 30 mg per person per day, respectively.

Administration does not necessarily have to be once daily, but may be divided into 3 to 4 administrations per day. The various forms of drug preparation can be administered by a route suited to the form of preparation, such as intravenously, intramuscularly, subcutaneously, intradermally or intraperitoneally in the case of an injection or orally in the case of a solid drug preparation.

The drug composition of the present invention can be used to suppress cholesterol re-elevation in patients with high cholesterol or pre-high cholesterol and preferably in patients with high cholesterol or pre-high cholesterol who are undergoing cholesterol-lowering treatment, particularly during a rest period in such treatment. Specifically, the drug composition of the present invention is preferably used in conjunction with or in alternation with cholesterol-lowering treatment in patients with high cholesterol (those with hypercholesterolemia or borderline hypercholesterolemia, those suffering from arteriosclerosis or conditions or diseases stemming from arteriosclerosis). Cholesterol-lowering treatment here may include dietary therapy and exercise therapy, but preferably involves administration of cholesterol-lowering drugs. Cholesterol-lowering drugs include known drugs and those that may be developed in the future, and examples of known cholesterol-lowering drugs include HMG-CoA reductase inhibitors, preferably pravastatin, simvastatin, fluvastatin and other statin drugs.

More preferably, the drug composition of the present invention is used during a rest period in cholesterol-lowering treatment and particularly a rest period in administration of a statin drug or other cholesterol-lowering drug in patients with high cholesterol who are undergoing cholesterol-lowering treatment. With this method of use, re-elevation of cholesterol during a rest period in cholesterol-lowering treatment can be suppressed over the long term without any particular dietary restrictions, with the result that blood cholesterol levels can be maintained within an appropriate range. In this way, the progress of conditions caused by high cholesterol can be prevented while reducing the administration frequency of cholesterol-lowering drugs. The occurrence of side-effects caused by these drugs can also be reduced.

(2-2) Food Composition and Use

The food composition provided by the present invention includes foods for specified health use (including qualified foods for specified health use) that have been given a cholesterol re-elevation-suppressing function, and foods for specified health use (including qualified foods for specified health use and invalid foods) used to prevent or ameliorate conditions and diseases caused by high cholesterol due to their cholesterol re-elevation-suppressing function. Moreover, the food composition of the present invention includes foods for specified health use (including qualified foods for specified health use and invalid foods) used to suppress re-elevation of cholesterol and prevent or improve conditions or diseases caused by high cholesterol in persons suffering from such conditions or diseases who are undergoing cholesterol-lowering treatment, particularly during a rest period in such treatment.

As discussed above, examples of conditions and diseases caused by high cholesterol include hypercholesterolemia (including hyper-LDL-cholesterolemia), arteriosclerosis and various diseases stemming from arteriosclerosis. Arteriosclerosis here also includes atherosclerosis. Examples of various diseases stemming from arteriosclerosis include cardiovascular diseases such as cerebral infarction and cerebral hemorrhage, and heart diseases such as cardiac infarction and angina.

The aforementioned foods for specified health use that have been given a cholesterol re-elevation suppressing function are those containing the edible protein hydrolysate and particularly the globin proteolysate or the peptide (Val-Val-Tyr-Pro) (SEQ ID NO: 1) in an amount sufficient to produce a cholesterol re-elevation suppressing effect, the effects of which (cholesterol re-elevation suppressing effects) are described on the food package of advertisement therefor.

Moreover, foods for specified health use that are used to prevent or ameliorate conditions or diseases caused by high cholesterol are those that contain the edible protein hydrolysate and particularly the globin proteolysate or the peptide (Val-Val-Tyr-Pro) (SEQ ID NO: 1) in an amount sufficient to produce a cholesterol re-elevation-suppressing effect, the effects of which (for example, preventative or ameliorative effects for hypercholesterolemia (or hyperlipidemia caused by high cholesterol), preventative or ameliorative effects against arteriosclerosis, etc.) are described on the food package or advertisement.

Moreover, foods for specified health use used to suppress re-elevation of cholesterol and prevent or improve conditions or diseases caused by high cholesterol in persons suffering from such conditions or diseases who are undergoing cholesterol-lowering treatment, particularly during a rest period in such treatment, are those containing the edible protein hydrolysate and particularly the globin proteolysate or the peptide (Val-Val-Tyr-Pro) (SEQ ID NO: 1) in an amount sufficient to produce a cholesterol re-elevation suppressing effect, the recipients and effects of which (with recipients being for example those suffering from conditions or diseases caused by high cholesterol who are undergoing cholesterol-lowering treatment or are in a rest period following cholesterol-lowering treatment, and effects being for example cholesterol re-elevation suppression effects, prevention or amelioration of hypercholesterolemia (or hyperlipidemia due to high cholesterol), prevention or amelioration of arteriosclerosis, etc.) are described on the food package or advertisement.

The food composition of the present invention may consist only of such the edible protein hydrolysate, particularly the globin proteolysate or the peptide (Val-Val-Tyr-Pro) (SEQ ID NO: 1).

The food composition of the present invention may also be one containing the edible protein hydrolysate and particularly the globin proteolysate or the peptide (Val-Val-Tyr-Pro) (SEQ ID NO: 1) in an amount sufficient to produce a cholesterol re-elevation suppressing effect. In this case, it can be prepared together using carriers or additives that can be used in foods together with the active component. This food composition includes supplements comprising the edible protein hydrolysate and particularly the globin proteolysate or the peptide (Val-Val-Tyr-Pro) (SEQ ID NO: 1) prepared together with acceptable carriers or additives as necessary in the form of tablets, pills, capsules, granules, powders or solutions (drinks). In this case, the proportion of the edible protein hydrolysate and particularly the globin proteolysate or the peptide (Val-Val-Tyr-Pro) (SEQ ID NO: 1) is not particularly limited but may normally be about 0.5% to less than 100% by weight or about 0.005% to less than 100% by weight, respectively.

The food composition of the present invention also includes ordinary drinks and foods compounded with the edible protein hydrolysate and particularly the globin proteolysate or the peptide (Val-Val-Tyr-Pro) (SEQ ID NO: 1).

Examples of drinks and foods include milk drinks, lactobacillus drinks, soft drinks containing juice, soft drinks, carbonated drinks, juice drinks, vegetable drinks, vegetable and fruit drinks, alcoholic drinks, powdered drinks, coffee drinks, black tea drinks, green tea drinks, barley tea drinks and other drinks; custard pudding, milk pudding, soufflé pudding, pudding with fruit juice and other puddings, jelly, Bavarian cream, yogurt and other desserts; ice cream, ice milk, lacto-ice, milk ice cream, ice cream with fruit, soft ice cream, ice candy, sherbet, popsicles and other iced desserts; chewing gum, bubble gum and other gums (stick gum, sugar-coated pellet gum); chocolates such as marble chocolate and other coated chocolates and strawberry chocolate, blueberry chocolate, melon chocolate and other flavored chocolates; hard candy (including bonbons, butterballs and marbles), soft candy (including caramels, nougat, gummies and marshmallows), drops, toffees and other candies; hard biscuits, cookies, rice crackers, crackers and other baked snacks (The listed above are snacks); consommé, potage and other soups; strawberry jam, blueberry jam, marmalade, apple jelly, apricot jam, and other jams; red wine and other fruit wines; processed fruits such as cherries, apricots, apples, strawberries and peaches in syrup; ham, sausage, roast pork and other processed meat products; fish ham, fish sausage, ground fish meat, boiled fish paste, fish paste balls, fish cake, fried fish balls, fish omelets, whale bacon and other processed seafood products; udon, cold wheat noodles, somen, buckwheat noodles, Chinese buckwheat noodles, spaghetti, macaroni, rice noodles, bean sticks, wontons and other noodles; and various other processed foods including side-dishes and mashed and seasoned fish and the like, as well as condiments such as soy sauce and other sauces, ketchup, mayonnaise and other dressings and noodle broth and the like. Drinks and snacks are preferred.

There are no particular limits on the amount of the active component (edible protein hydrolysate, particularly the globin proteolysate or the peptide (Val-Val-Tyr-Pro) (SEQ ID NO: 1)) contained in this food composition, or on the amount ingested, which may be selected from a wide range according to the type of food composition, the degree of improvement desired and other conditions. The ingested amount differs depending on the type of food composition, but can be selected appropriately from the range of about 100 to 3000 mg/60 kg per ingestion for the globin proteolysate or about 1 to 30 mg/60 kg per ingestion for the peptide (Val-Val-Tyr-Pro) (SEQ ID NO: 1).

The food composition of the present invention has a cholesterol re-elevation suppressing effect attributable to the edible protein hydrolysate, particularly the globin proteolysate or the peptide (Val-Val-Tyr-Pro) (SEQ ID NO: 1), included as a component therein, and has the effect of improving high cholesterol due to re-elevation of cholesterol. Consequently, the food composition of the present invention can be used effectively as a composition for suppressing cholesterol re-elevation and maintaining blood cholesterol values at appropriate levels, or as a composition for preventing the occurrence or progress of various conditions or diseases stemming from high cholesterol, or for ameliorating such conditions or diseases.

The food composition of the present invention can be used with the aim of suppressing cholesterol re-elevation in people with high cholesterol or pre-high cholesterol. In particular, the food composition of the present invention is preferably used in conjunction with or in alternation with cholesterol-lowering treatment, in people who have high cholesterol (those with hypercholesterolemia or borderline hypercholesterolemia or those with arteriosclerosis or conditions or diseases stemming from arteriosclerosis) and who are undergoing cholesterol-lowering treatment. Cholesterol-lowering treatment here may include dietary therapy and exercise therapy, but preferably involves medical treatment such as administration of cholesterol-lowering drugs. Cholesterol-lowering drugs include known drugs and those that may be developed in the future, and examples of known cholesterol-lowering drugs include HMG-CoA reductase inhibitors, preferably pravastatin, simvastatin, fluvastatin and other statin drugs.

More preferably, the drug composition of the present invention is used during a rest period in cholesterol-lowering treatment and particularly a rest period in administration of a statin drug or other cholesterol-lowering drug in patients with high cholesterol who are undergoing cholesterol-lowering treatment. With this method of use, re-elevation of cholesterol over time due to interruption of cholesterol-lowering treatment can be suppressed over the long term, with the result that blood cholesterol levels can be maintained within an appropriate range. In this way, the progress of conditions caused by high cholesterol can be prevented while reducing the frequency of administration of statin drugs. The occurrence of side-effects caused by these drugs can also be reduced.

(2-3) Feed Composition and Use

The feed composition provided by the present invention includes feeds that have been given a cholesterol re-elevation suppressing function, and feeds used to prevent or ameliorate conditions and diseases caused by high cholesterol due to their cholesterol re-elevation suppressing function. This feed can be used favorably as pet food for dogs, cats and the like in particular. The aforementioned feeds that have been given a cholesterol re-elevation suppressing function contain the edible protein hydrolysate and particularly the globin proteolysate or the peptide (Val-Val-Tyr-Pro) (SEQ ID NO: 1) in an amount sufficient to suppress re-elevation of cholesterol. The feeds used to prevent or ameliorate conditions and diseases caused by high cholesterol also contain the edible protein hydrolysate and particularly the globin proteolysate or the peptide (Val-Val-Tyr-Pro) (SEQ ID NO: 1) in an amount sufficient to suppress re-elevation of cholesterol.

This feed composition includes those comprising the edibel protein hydrolysate and particularly the globin proteolysate or the peptide (Val-Val-Tyr-Pro) (SEQ ID NO: 1) prepared in the form of tablets, pills, capsules, granules, powders or solutions together with carriers or additives that can be compounded with feed as necessary, as well as those in the form of ordinary feed compounded with the edible protein hydrolysate and particularly the globin proteolysate or the peptide (Val-Val-Tyr-Pro) (SEQ ID NO: 1).

The amount of the active component (edible protein hydrolysate, particularly globin proteolysate or peptide (Val-Val-Tyr-Pro) (SEQ ID NO: 1)) compounded in the feed composition or the ingested amount is not particularly limited, and can be selected appropriately within a wide range according to the type of animals ingesting the feed and the desired ameliorative effects and degree thereof as well as other conditions. The ingested amount differs depending on the type of feed composition but can be selected appropriately from the range of about 50 to 1000 mg/10 kg per ingestion for the food protein hydrolysate, particularly the globin proteolysate or about 0.5 to 10 mg/10 kg per ingestion for the peptide (Val-Val-Tyr-Pro) (SEQ ID NO: 1).

The feed composition of the present invention can be used with the aim of suppressing cholesterol re-elevation in animals with high cholesterol or pre-high cholesterol. In particular, the feed composition of the present invention is preferably used in conjunction with or in alternation with cholesterol-lowering treatment in animals with high cholesterol. Cholesterol-lowering treatment here may include dietary therapy and exercise therapy, but preferably involves medical treatment such as administration of cholesterol-lowering drugs. More preferably, the feed composition of the present invention is administered to animals with high cholesterol during a rest period in cholesterol-lowering treatment. With this method of use, re-elevation of cholesterol over time due to interruption of cholesterol-lowering therapy can be suppressed over the long term, with the result that blood cholesterol levels can be maintained in an appropriate range.

EXAMPLE

Preparation Examples and Test Examples are given below to illustrate the invention in more detail, but the scope of the invention is not limited by these examples. In the following Test Examples, "%" represents "percent by weight", unless specified otherwise.

Preparation Example 1

Preparation of Globin Proteolysate

A method for preparing a globin proteolysate using bovine erythrocyte is described below in detail.

To 100 kg of fresh bovine erythrocytes was added 250 liters of water to allow sufficient hemolysis. After adjustment of the pH to 2.8 with phosphoric acid, $2.6 \times 10^7$ units of acid protease from *Aspergillus niger* were added to the solution and reacted at 50° C. for 3 hours.

After the reaction, the reaction solution was heated at 80° C. for 30 minutes to terminate the reaction. Thereafter, an aqueous suspension of calcium hydroxide was added to the reaction solution to adjust the pH to 6.5. Then, 10 kg of diatomaceous earth was added, and the mixture was filtered with a filter press. The resulting filtrate was spray-dried, thereby producing 23 kg of a globin proteolysate as a powder. The molecular weight distribution of the globin proteolysate was examined by gel filtration chromatography performed under the following conditions.

Figure 1:
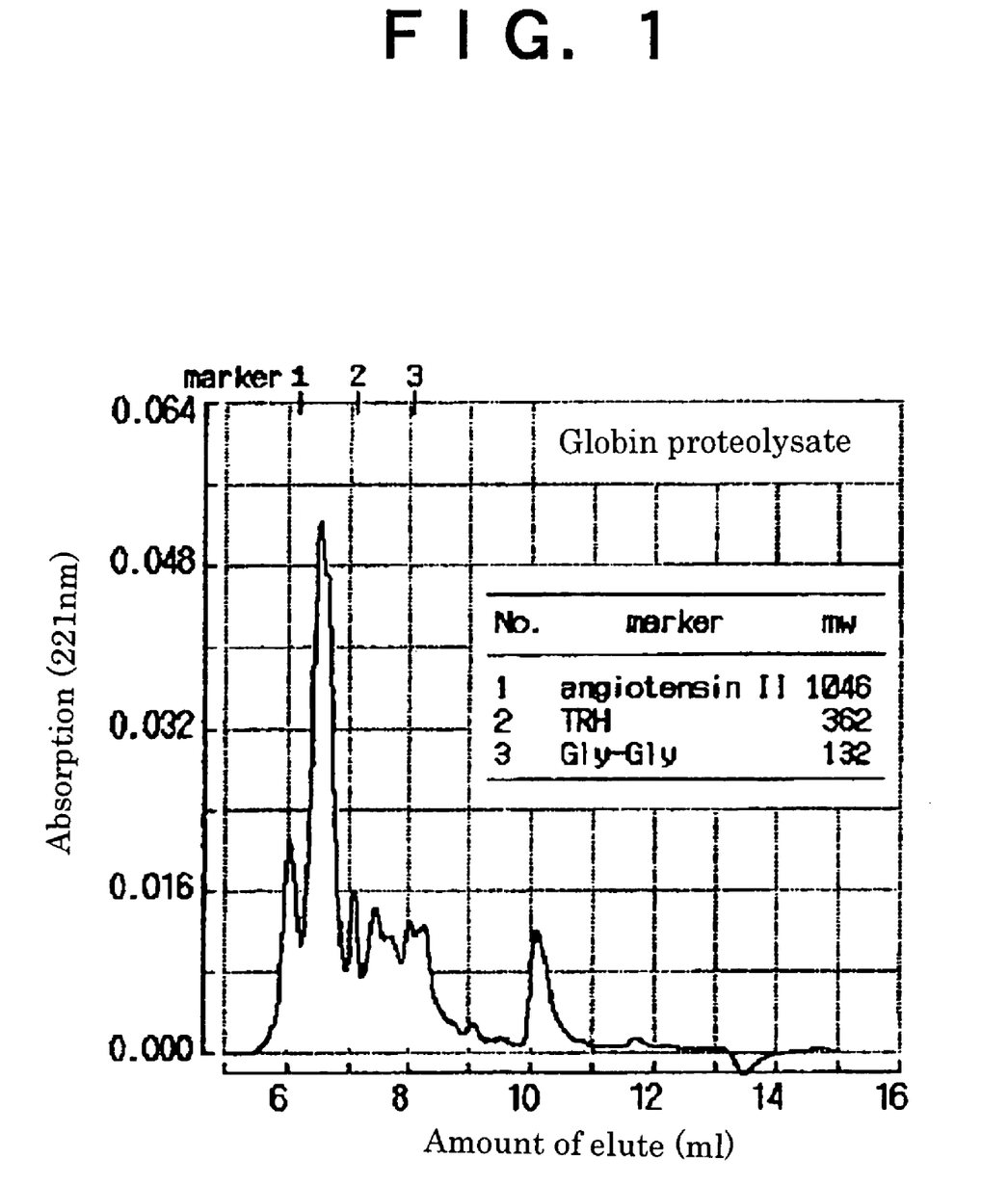
FIG. 1 shows a gel filtration chromatogram of a globin proteolysate (Preparation Example 1).

<Gel Filtration Chromatography>
Equipment: High-performance liquid chromatograph (Shimadzu Corporation, Model LC-6A)
Column: PolyHYDROXYETHYL A, 5 μm, 9.4×200 mm, manufactured by PolyLC Inc.
Eluate: 50 mM Formic acid
Flow rate: 0.5 ml/min
Detection: UV absorption at 221 nm FIG. 1 shows a gel filtration chromatogram of a globin proteolysate obtained according to the above-described gel filtration chromatography.

Preparation Example 2

Manufacture of Casein Hydrolysate

A method for preparing a casein hydrolysate using casein is given here.

5500 liters of water were added to 500 kg of casein, a calcium hydroxide solution was added and thoroughly dissolved to adjust the pH to 8.0 to 8.5, and alkaline protease was added and reacted for 3 hours at 60° C.

After the reaction, the reaction liquid was heated at 80° C. for 30 minutes to terminate the reaction, diatomaceous earth was added, the mixture was filtered with a filter press, and the resulting filtrate was spray dried to obtain 450 kg of casein hydrolysate powder.

Preparation Example 3

Fractionation and purification of peptide that suppreses a re-elevationin of cholesterol The peptide of the present invention was obtained through the following procedures: (1) ion exchange, (2) ultrafiltration, (3) separation by reverse phase column chromatography under acidic conditions, and (4) separation by reverse phase chromatography under neutral conditions.

(1) Ion Exchange

A 10% aqueous solution containing 13.7 g of the globin proteolysate obtained in Preparation Example 1 was introduced to a weakly acidic cation exchange resin (Amberlite $IRC_{50}$, $H^+$ Type, Organo Co., Ltd.) and stirred for 1 hour for adsorption. An unadsorbed fraction was thereby separated.

(2) Ultrafiltration

The unadsorbed fraction obtained by the aforementioned ion exchange was subjected to ultrafiltration using a stirring-force ultrafilter unit (manufactured by Advantec, UHP 90K) and a ultrafilter membrane (manufactured by Advantec, UIIH-1, molecular weight cutoff: 1000). The liquid remaining on the ultrafilter membrane (residual liquid) was collected. The fraction thus obtained was subjected to acid hydrolysis and quantified according to a ninhydrin method. The acid hydrolysis was carried out by placing 1 ml of hydrochloric acid having a final concentration of 6 N into a test tube per 3 to 5 mg of protein, sealing the tube under atmospheric pressure and heating it at 110° C. for 22 hours. The aforementioned ninhydrin method was performed as follows. The pH of the specimen after hydrolysis was adjusted to 5.0 with sodium hydroxide. The specimen was then reacted with a ninhydrin reagent dissolved in a 0.2 M citrate buffer (pH 5.0) at 100° C. for 15 minutes. Absorbance at 570 nm was measured. Separately, aqueous L-leucine solutions (75, 150, 225, and 300 nmol/ml) were subjected to a ninhydrin reaction as standard solutions. A calibration curve was obtained from the absorbances measured, and the amount of amino groups equivalent to L-leucine in the specimen was calculated. The result of the quantification is presented in Table 1. The yield based on the starting globin proteolysate is also presented in Table 1.

(3) Reverse Phase (Acid) Chromatography

The filtrate obtained after the ultrafiltration above was subjected to reverse phase (acid) chromatography under the following conditions.

<Reverse Phase (Acid) Chromatography>

Equipment: High performance liquid chromatograph (Shimadzu Corporation, Model LC-10A)

Column: SuperPac Pep-S, 15 µm, 22.5×250 mm, manufactured by Pharmacia

Eluate: Aqueous acetonitrile solution containing 0.1% trifluoroacetic acid

Linear concentration gradient of acetonitrile from 2 to 35%; Acetonitrile concentration was changed at a rate of 1%/min Flow rate: 5 ml/min Temperature: 40° C.

Detection: UV absorption at 220 nm

Fractioning Time: 53.8 to 54.5 minutes (Fraction A)

Figure 2:
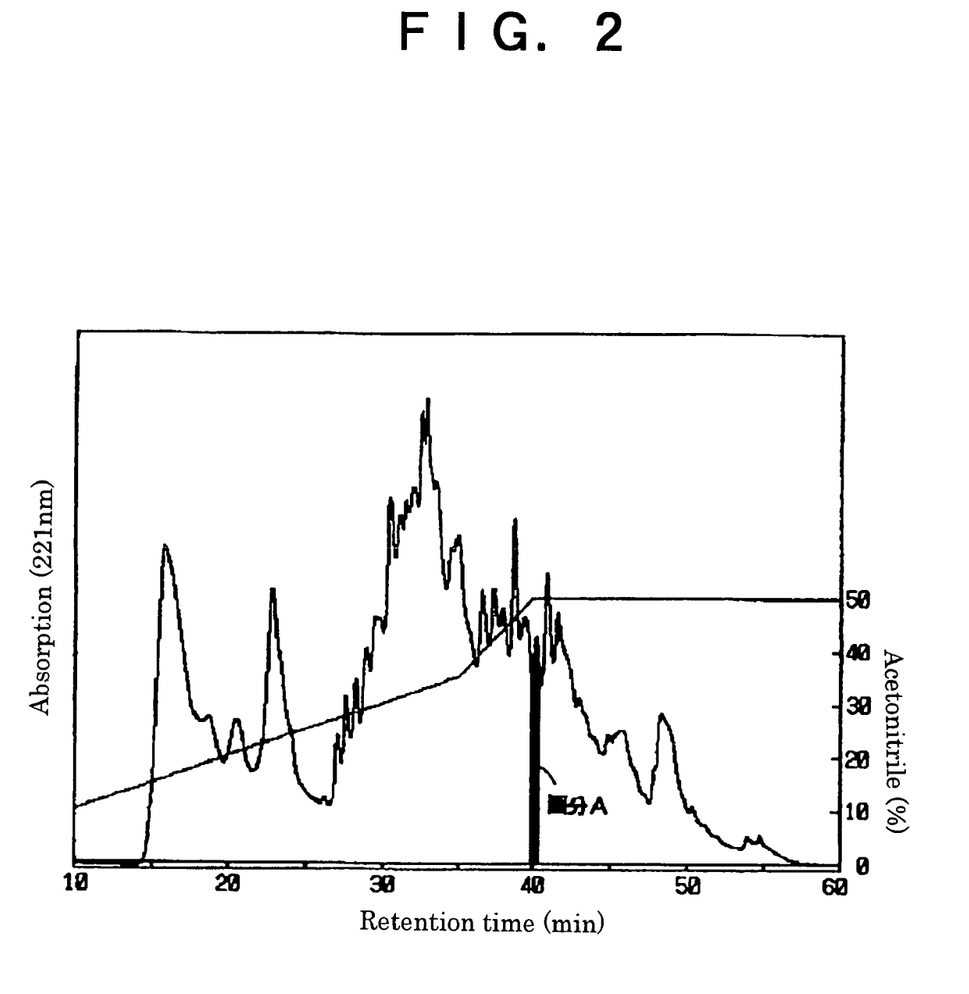
FIG. 2 shows the result (chromatogram) of reverse phase (acid) chromatography performed in Preparation Example 3(3).

FIG. 2 shows a chromatogram obtained by the above-described reverse phase (acid) chromatography.

The fraction thus obtained was subjected to acid hydrolysis and then quantified by amino acid analysis. Acid hydrolysis was carried out by placing 1 ml of hydrochloric acid (final concentration of 6 N HCl) into a test tube per 3 to 5 mg of protein, sealing the test tube under reduced pressure, and heating it at 110° C. for 22 hours. Amino acid analysis was conducted under the following conditions.

<Amino Acid Analysis>

Equipment: High performance liquid chromatograph (Shimadzu Corporation, Model LC-6A)

Column: Shim-pack ISC-07/S1504 Na, 7 µm, 4.0×150 mm, manufactured by Shimadzu Corporation Eluate: Amino acid mobile phase kit (Na type) manufactured by Shimadzu Corporation Flow rate: 0.3 ml/min Temperature: 55° C.

Reaction solution 1: Analysis kit OPA reagent manufactured by Shimadzu Corporation Detection: Fluorescence absorption (Ex 348 nm, Em 450 nm)

The acid-hydrolyzed solution was concentrated, dried and caked using a rotary evaporator, and further dried under reduced pressure for more than 12 hours, thereby completely removing hydrochloric acid. The resultant was dissolved in 0.2 M citrate buffer (pH 2.2) such that each amino acid was contained in a proportion of about 100 nmol/ml. This solution was filtered through a 0.45 µm filter, and 10 µl of the filtrate was introduced into the column. For a standard solution, an 18-component type-H amino acid mixed standard solution (Wako Pure Chemical Industries, Ltd.) was diluted 25-fold with 0.2 M citrate buffer (pH 2.2), and 10 µl of the diluted solution was introduced into the column (1 nmol/10 µl for each amino acid). The peak areas of the amino acids were calculated and analyzed using Chromatopac C-R4A (Shimadzu Corporation), and the amounts of amino acids were calculated based on the ratios of the peak areas for the specimen to the peak areas for the standard solution. The results are shown in Table 1. The yield based on the globin proteolysate is also presented in Table 1.

(4) Reverse Phase (Neutral) Chromatography

The fraction eluted and fractioned by the above-described reverse phase (acid) chromatography was further subjected to reverse phase (neutral) chromatography under the following conditions.

<Reverse Phase (Neutral) Chromatography>

Equipment: High performance liquid chromatograph (Shimadzu Corporation, Model LC-10A)

Column: SuperPac Pep-S, 15 µm, 22.5×250 mm, manufactured by Pharmacia

Eluate: Aqueous acetonitrile solution containing 20 mM ammonium acetate buffer (pH 6.5)

Linear concentration gradient of acetonitrile from 0 to 25%; Acetonitrile concentration was changed at a rate of 0.5%/min Flow rate: 5 ml/min Temperature: 40° C.

Detection: UV absorption at 220 nm

Fractioning Times: 41.7 to 43.2 minutes (Fraction B), 45.8 to 51.0 minutes (Fraction C).

Figure 3:
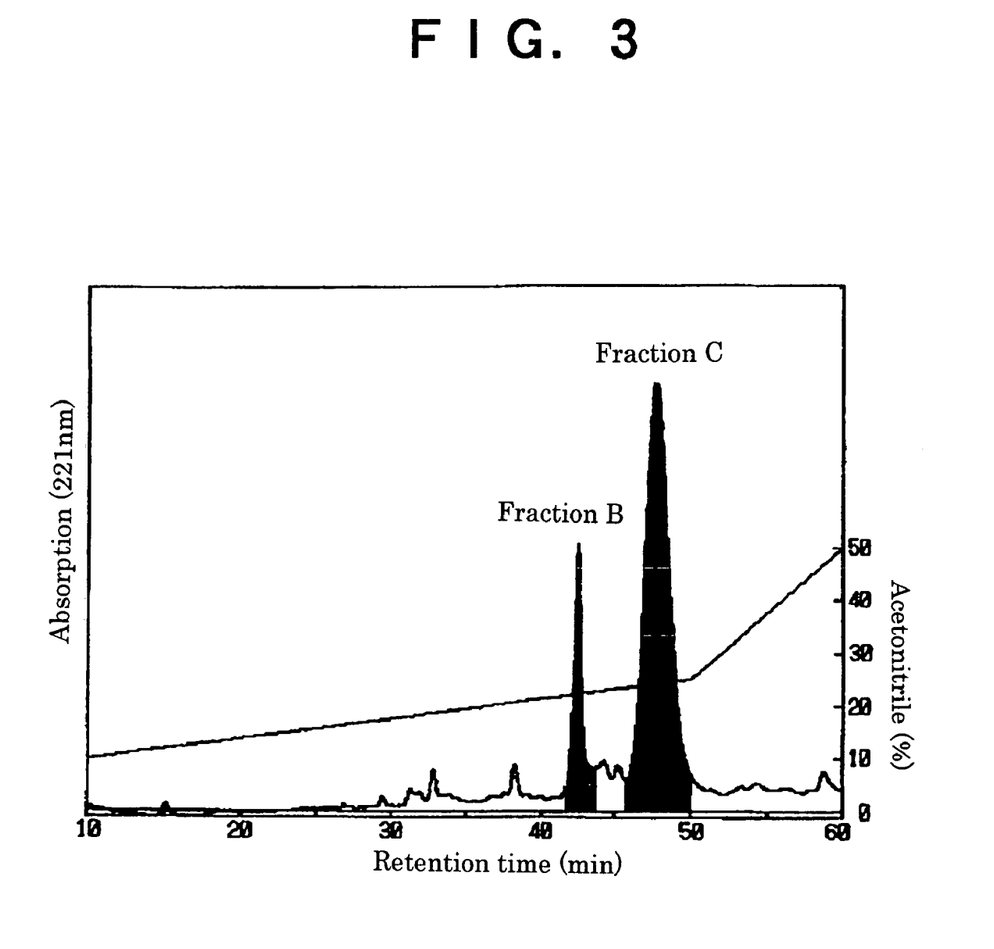
FIG. 3 shows the result (chromatogram) of reverse phase (neutral) chromatography performed in Preparation Example 3(4).

FIG. 3 shows a chromatogram obtained by the reverse phase (neutral) chromatography described above. The resulting fractions were quantified as in (3) above, and then identified. The amino acid composition was computed based on the proportion of each amino acid relative to the total amino acid content. The results showed that Fraction B was VTL (Val-Thr-Leu), and Fraction C was VVYP (Val-Val-Tyr-Pro) (SEQ ID NO:1). Matching with the amino acid sequence of hemoglobin verified that these fractions are present in hemoglobin. The results of the quantification are presented in Table 1 together with the yields based on the globin proteolysate.

TABLE 1

| Peptide | Amount of protein (g) | Yield (%) |
|---|---|---|
| Globin proteolysate | 13.70 | 100.0 |
| Ion exchange + Ultrafiltration Reverse phase chromatography | 4.24 | 30.9 |
| Fraction A | 0.39 | 0.28 |
| Fraction B VTL | 0.009 | 0.06 |
| Fraction C VVYP (SEQ ID NO: 1) | 0.006 | 0.04 |

Test Example 1

Cholesterol Re-elevation Suppression Effects

The cholesterol-lowering effects of statin drugs are dramatic, but many side effects have been reported. Consequently, rather than using statin drugs over the long term, it is desirable to lower cholesterol to appropriately levels by statin drug administration, and then immediately stop the drug and maintain the lowered cholesterol levels with dietary therapy. However, it is difficult for patients to stick to dietary therapy, and most give up part way through. Strict limitations on diet are also undesirable from the standpoint of quality of life (QOL).

In this test, the cholesterol re-elevation suppressing effects of the globin proteolysate of the present invention and in particular the cholesterol re-elevation suppressing effects during a statin drug rest period were investigated with respect to 6 patients with high cholesterol.

Specifically, statin drug (pravastatin) administration (4 weeks) was interrupted and the patients were given a soft drink (see Example 1 (1)) containing the globin proteolysate obtained in Preparation Example 1 twice a day for 42 days (ingested amount=2 g of globin proteolysate per day). During this period no statin drug was administered, and there were no dietary restriction.

Figure 4:
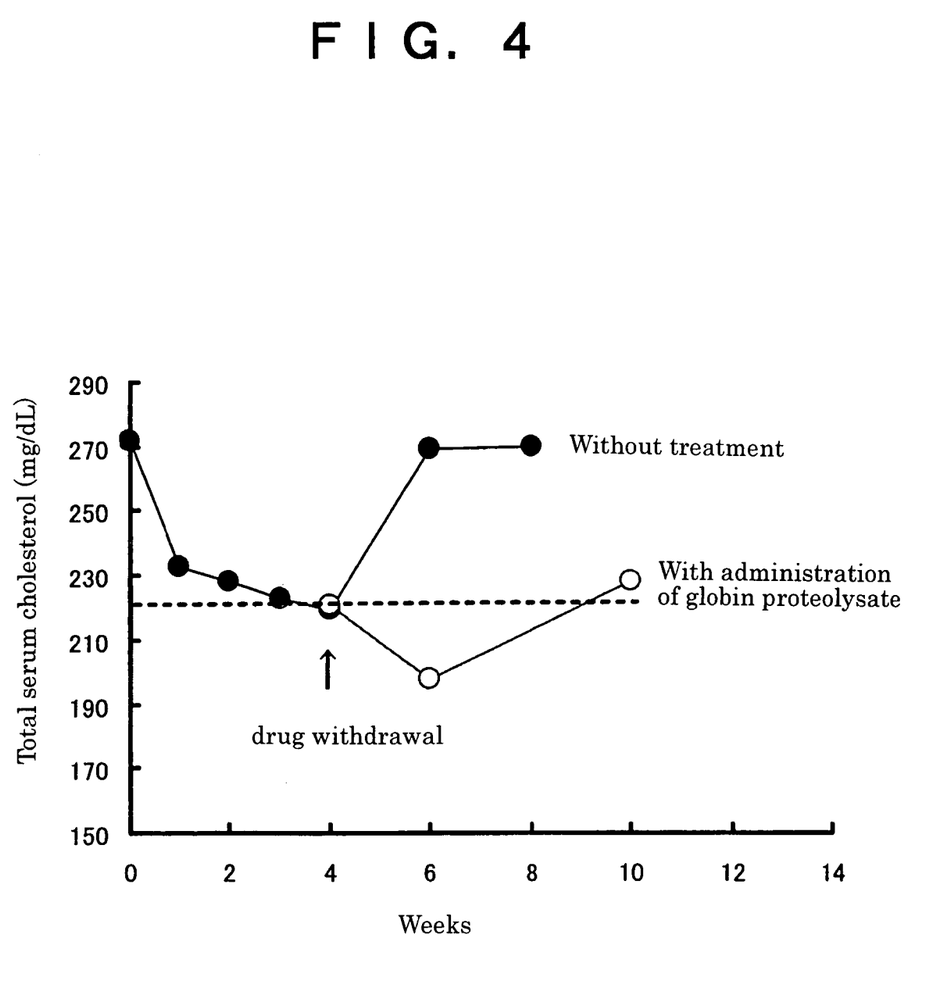
FIG. 4 compares changes in total serum cholesterol after interruption of pravastatin administration either without treatment (black dot) or with administration of a globin proteolysate (white dot) (Test Example 1). The dotted line in the figure indicates the upper limit of normal total cholesterol.
Figure 5:
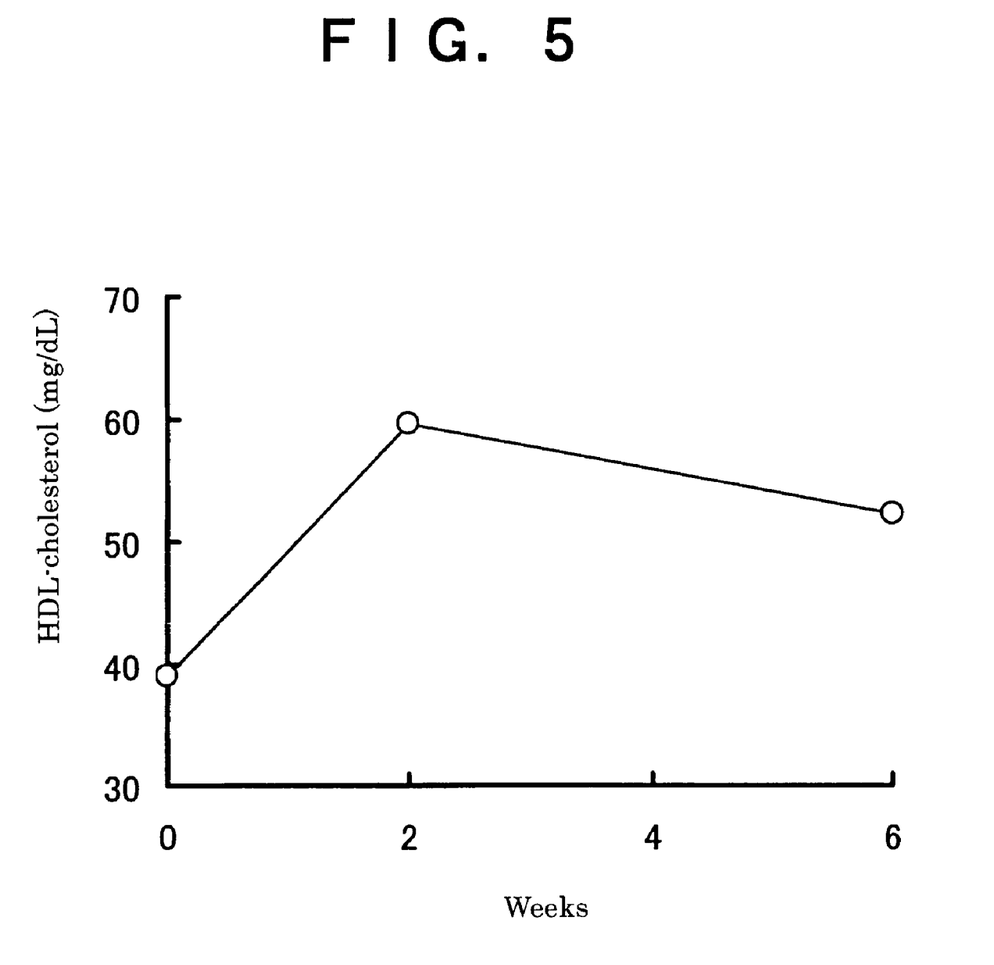
FIG. 5 shows the effect of globin proteolysate administration on HDL-cholesterol following interruption of pravastatin administration (Test Example 1).

Blood was collected immediately after interruption of pravastatin, after 14 days and after 42 days, and total cholesterol and HDL cholesterol in serum were measured. These test results are shown in FIGS. 4 and 5, respectively. The dots in the figures indicate average results for the 6 patients.

As shown in FIG. 4, in the group receiving no globin proteolysate (untreated group, black dots) total cholesterol became re-elevated after interruption of pravastatin, returning to pre-administration levels (rebound effect).

In the group receiving the globin proteolysate (white dots), however, total cholesterol did not become re-elevated and remained within the normal range (near 220 mg/dl) after interruption of pravastatin even without dietary restrictions (FIG. 4). Levels of HDL-cholesterol (good cholesterol) tended to rise (FIG. 5).

This shows that the globin proteolysate of the present invention has the effect of suppressing cholesterol re-elevation. In particular, the globin proteolysate of the present invention is effective in suppressing cholesterol re-elevation over the long term without dietary restrictions when used during a rest period following statin drug administration. This shows that rest periods in statin drug administration can be prolonged while maintaining ordinary diet and QOL through the use of the globin proteolysate of the present invention, resulting in a lower occurrence of side-effects.

Test Example 2

Safety Test

The globin proteolysate prepared in Preparation Example 1 was orally administered to male and female ICR mice in an amount of 10 g/kg (maximum allowable dose) or greater, and there were no fatalities, thereby establishing the safety of the peptide.

Example 1

Preparation of Foods Containing Edible Protein Hydrolysates, Specifically Globin Proteolysates (1) Preparation of Soft Drink A soft drink was prepared according to the following recipe.

| (Soft Drink Recipe) | |
|---|---|
| Reduced maltose syrup | 50 kg |
| Erythritol | 50 kg |
| Globin proteolysate | 20 kg |
| Acid flavoring | 2 kg |
| Preservative | 0.1 kg |
| Flavoring | Trace |
| Purified water | As needed |
| Total | 1000 L |

50 kg of reduced maltose syrup and 50 kg of erythritol were dissolved in about 800 liters of purified water, and 20 kg of globin proteolysate, 2 kg of acid flavoring and 0.1 kg of preservative were added in that order and completely dissolved, after which purified water was added to a total of 1000 liters to obtain a soft drink.

(2) Preparation of Chocolate

Fifty milligrams of the casein hydrolysate prepared in Preparation Example 2 was added to 100 g of chocolate, thereby giving a chocolate having a function of suppressing a re-elevation of cholesterol.

(3) Preparation of Green Tea Beverage

Eight kilograms of green tea leaves were introduced to 300 liters of hot water (80° C.) and extracted at that temperature for 4 minutes. The resulting extract was cooled and centrifuged. Clear supernatant was collected as a green tea extract. To this extract were added 0.4 kg of vitamin C and then 10 kg of the globin proteolysate prepared in Preparation Example 1. Hot water was added to attain the final volume of 1000 liters. The mixture was heated to 85° C. or higher, charged into a metal can, and retort-sterilized (125° C., 5 minutes), thereby giving a green tea beverage.

(4) Preparation of Chewing Gum

A chewing gum was prepared using the formulation below.

<Chewing gum formulation>

| | |
|---|---|
| Gum base | 25.0 parts by weight |
| Sucrose | 63.8 parts by weight |
| Corn syrup | 10.0 parts by weight |
| Glycerol | 1.0 part by weight |
| Peptide (VVYP) (SEQ ID NO: 1) | 0.2 parts by weight |
| Total | 100.0 parts by weight |

Gum base, sugar, corn syrup and glycerol were mixed first. The globin proteolysate prepared in Preparation Example 1 was then added, and the mixture was uniformly kneaded using a mixer at 50° C. After cooling, the mixture was press-molded by a roller, thereby giving a chewing gum stick containing, as an active ingredient, the globin proteolysate in a proportion of 300 mg per stick.

(5) Supplement

The following ingredients were kneaded, granulated, dried, and tableted according to a standard method, thereby producing tablets containing, as an active ingredient, globin proteolysate in an amount of 65% (200 mg) per tablet (310 mg). These tablets are for use as supplements having pharmacological function of suppressing a re-elevation of cholesterol, resulting from the globin proteolysate.

| <Tablet formulation> | (per tablet) |
|---|---|
| Globin proteolysate (Preparation Example 1) | 200 mg |
| Lactose | 100 mg |
| Sucrose fatty acid ester | 10 mg |
| Total | 310 mg |

(6) Feed

The globin proteolysate prepared in Preparation Example 1 was added in a proportion of 10% to a premix containing vitamins, minerals and the like. This mixture was added to a commercially available dog food in a proportion of 10%, thereby producing a dog food having a function of suppressing a re-elevation of cholesterol.

Example 2

Preparation of Peptide (Val-Val-Tyr-Pro) (SEQ ID NO: 1)-Containing Food (1) Supplement The following ingredients were kneaded, granulated, dried, and tableted according to a standard method, thereby producing tablets containing, as an active ingredient, Val-Val-Tyr-Pro (SEQ ID NO: 1) in an amount of 1% (2 mg) per tablet (200 mg). These tablets are for use as supplements having a function of suppressing a re-elevation of cholesterol resulting from the Val-Val-Tyr-Pro (SEQ ID NO: 1).

| <Tablet formulation> | (per tablet) |
|---|---|
| Val-Val-Tyr-Pro | 2 mg |
| Sorbitol | 188 mg |
| Sucrose fatty acid ester | 10 mg |
| Total | 200 mg |

(2) Feed

The peptide having the amino acid sequence Val-Val-Tyr-Pro (SEQ ID NO: 1) prepared in Preparation Example 3 was added in a proportion of 0.1% to a premix containing vitamins, minerals and the like. This mixture was added to a commercially available dog food in a proportion of 10%, thereby producing a dog food having a function of suppressing a re-elevation of cholesterol.

INDUSTRIAL APPLICABILITY

With the present invention a drug composition, food composition and feed composition having the effect of suppressing re-elevation of cholesterol can be provided through the inclusion as an active component of an edible protein hydrolysate and particularly a globin proteolysate or a peptide (Val-Val-Tyr-Pro) (SEQ ID NO: 1). Due to their cholesterol re-elevation suppression effects, these compositions have the effect of suppressing re-elevation of cholesterol and maintaining appropriate cholesterol levels in patients with high cholesterol or pre-high cholesterol, particularly during drug rest periods in those who are undergoing cholesterol-lowering treatment. As a consequence, the compositions of the present invention can be used to effectively prevent or treat conditions and diseases caused by high cholesterol, specifically hypercholesterolemia, arteriosclerosis and various conditions and diseases stemming therefrom.

The useful effects described below can be obtained by applying the compositions and methods provided by the present invention to patients with high cholesterol who are receiving cholesterol-lowering treatment by means of statin drugs and other HMG-COA reductase inhibitors during the drug rest period of such treatment:

(1) Blood cholesterol re-elevation can be suppressed during the rest period, and blood cholesterol values maintained at an appropriate level over the long term;

(2) As a result, the rest period for statin drugs can be prolonged (reducing the frequency of statin drug administration), thereby reducing the rate of occurrence of side effects due to statin drug administration.

These results can be obtained during the rest period in statin drug treatment without low-cholesterol diets or other dietary restrictions, so the present invention can contribute to improving the quality of life of patients with high cholesterol.

What is claimed is:

1. A method for suppressing re-elevation of total cholesterol and increasing HDL cholesterol in a patient with high cholesterol, comprising the steps of:
- administering a cholesterol-lowering treatment to the patient;
- interrupting the cholesterol-lowering treatment to provide a rest period; and
- administering to the patient a composition comprising a globin proteolysate or a peptide consisting of Val-Val-Tyr-Pro (SEQ ID NO: 1) in a quantity sufficient to produce cholesterol re-elevation suppressing effects, during the rest period following the cholesterol-lowering treatment for the patient.

2. The method according to claim 1, wherein the patient is a coronary disease patient, and
the method being for maintaining a level of total cholesterol in blood at or below the upper limit of the normal range for total cholesterol by suppressing re-elevation of total cholesterol.

3. The method according to claim 1, wherein the cholesterol-lowering treatment is a statin drug treatment.

4. The method according to claim 1, wherein the cholesterol-lowering treatment is a treatment conducted by administrating a HMG-CoA reductase inhibitor to the patient.

* * * * *